(12) United States Patent
Tripp et al.

(10) Patent No.: US 7,901,713 B2
(45) Date of Patent: *Mar. 8, 2011

(54) INHIBITION OF COX-2 AND/OR 5-LOX ACTIVITY BY FRACTIONS ISOLATED OR DERIVED FROM HOPS

(75) Inventors: Matthew L. Tripp, Gig Harbor, WA (US); Gary K. Darland, Gig Harbor, WA (US); Mark Fuller, Seatac, WA (US); John G. Babish, Brooktondale, NY (US); Jeffrey S. Bland, Fox Island, WA (US)

(73) Assignee: Metaproteomics, LLC, San Clemente, CA (US)

( * ) Notice: Subject to any disclaimer, the term of this patent is extended or adjusted under 35 U.S.C. 154(b) by 1717 days.

This patent is subject to a terminal disclaimer.

(21) Appl. No.: 10/866,315

(22) Filed: Jun. 10, 2004

(65) Prior Publication Data
US 2009/0118373 A1  May 7, 2009

Related U.S. Application Data (63) Continuation-in-part of application No. 10/689,856, filed on Oct. 20, 2003, now Pat. No. 7,270,835, which is a continuation-in-part of application No. 10/464,410, filed on Jun. 18, 2003, which is a continuation-in-part of application No. 10/400,293, filed on Mar. 26, 2003, now abandoned, and a continuation-in-part of application No. 10/401,283, filed on Mar. 26, 2003, now abandoned, application No. 10/866,315, which is a continuation-in-part of application No. 10/464,834, filed on Jun. 18, 2003, and a continuation-in-part of application No. 09/885,721, filed on Jun. 20, 2001, now Pat. No. 7,205,151.

(60) Provisional application No. 60/450,237, filed on Feb. 25, 2003, provisional application No. 60/420,383, filed on Oct. 21, 2002.

(51) Int. Cl.
*A01N 65/00* (2009.01)
(52) U.S. Cl. ...................................................... 424/725
(58) Field of Classification Search .................... None
See application file for complete search history.

(56) References Cited

U.S. PATENT DOCUMENTS

| | | | |
|---|---|---|---|
| 3,451,821 A | 6/1969 | Todd et al. |
| 3,552,975 A | 1/1971 | Worden et al. |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzer et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,296,637 A | 3/1994 | Stegink et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |
| 5,919,813 A | 7/1999 | De Juan |
| 5,968,539 A | 10/1999 | Beerse et al. |
| 6,020,019 A | 2/2000 | Ting et al. |
| 6,129,907 A | 10/2000 | Sreenivasan et al. |

(Continued)

FOREIGN PATENT DOCUMENTS

CN  1203268  12/1998

(Continued)

OTHER PUBLICATIONS

"Information on arthrotrimtm product", downloaded from Internet Aug. 30, 2002.
"Information on Zyflamend and Zyflamend PM", downloaded from Internet Aug. 30, 2002.
"Information on Hops and Beer Flavours", downloaded from internet Feb. 15, 2005.
Anto, et al. Pharm. Pharmacol. Comm. 4:103-106 (1998).
Bermejo, et al. Rev. Esp Enferm. Dig. 95: 621-624 and 625-628 (2003).

(Continued)

Primary Examiner — Michael V Meller
(74) Attorney, Agent, or Firm — McDermott Will & Emery, LLP (57) ABSTRACT

A natural formulation of compounds isolated or derived from hops which inhibit the activity of cyclooxygenase-2 (COX-2) and/or 5-lipoxygenase (5-LOX) is disclosed. The hops formulations may be administered to a mammal to treat or inhibit a pathological condition associated with the activity of COX-2 and/or 5-LOX in such a mammal.

15 Claims, 2 Drawing Sheets

U.S. PATENT DOCUMENTS

| | | |
|---|---|---|
| 6,200,594 B1 | 3/2001 | Ernest et al. |
| 6,210,701 B1 | 4/2001 | Darland et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Galcerá |
| 6,482,456 B1 | 11/2002 | Yokoo et al. |
| 6,492,429 B1 | 12/2002 | Graus et al. |
| 6,583,322 B1 | 6/2003 | Shalai et al. |
| 6,689,388 B2 | 2/2004 | Kuhrts |
| 6,790,459 B1 | 9/2004 | Cheng et al. |
| 6,801,860 B1 | 10/2004 | Dessen et al. |
| 7,144,590 B2 | 12/2006 | Kuhrts |
| 7,195,785 B2 | 3/2007 | Babish et al. |
| 7,205,151 B2 | 4/2007 | Babish et al. |
| 7,270,835 B2 | 9/2007 | Tripp et al. |
| 7,279,185 B2 | 10/2007 | Babish et al. |
| 7,332,185 B2 | 2/2008 | Babish et al. |
| 7,431,948 B2 | 10/2008 | Tripp et al. |
| 2002/0028852 A1 | 3/2002 | Ghai et al. |
| 2002/0076452 A1 | 6/2002 | Babish et al. |
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1 | 10/2002 | Nuss et al. |
| 2003/0003212 A1 | 1/2003 | Chien et al. |
| 2003/0008021 A1 | 1/2003 | Babish et al. |
| 2003/0035851 A1 | 2/2003 | Chen |
| 2003/0077313 A1 | 4/2003 | Schwartz et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0180402 A1 | 9/2003 | Jia et al. |
| 2003/0228369 A1 | 12/2003 | Kuhrts |
| 2004/0072900 A1 | 4/2004 | Artman et al. |
| 2004/0086580 A1 | 5/2004 | Tripp et al. |
| 2004/0115290 A1 | 6/2004 | Tripp et al. |
| 2004/0137096 A1 | 7/2004 | Kuhrts |
| 2004/0151792 A1 | 8/2004 | Tripp et al. |
| 2004/0219240 A1 | 11/2004 | Babish et al. |
| 2005/0042317 A1 | 2/2005 | Babish et al. |
| 2005/0129791 A1 | 6/2005 | Babish et al. |
| 2005/0191375 A1 | 9/2005 | Babish et al. |
| 2005/0192356 A1 | 9/2005 | Babish et al. |
| 2006/0127511 A1 | 6/2006 | Tripp et al. |
| 2006/0127512 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0233902 A1 | 10/2006 | Yajima et al. |
| 2007/0003646 A1 | 1/2007 | Kuhrts |
| 2007/0020352 A1 | 1/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2008/0127720 A1 | 6/2008 | Pauli et al. |
| 2008/0248131 A1 | 10/2008 | Tripp et al. |
| 2009/0118373 A1 | 5/2009 | Tripp et al. |

FOREIGN PATENT DOCUMENTS

| | | |
|---|---|---|
| DE | 1901277 | 8/1970 |
| DE | 2212148 | 9/1972 |
| DE | 3931147 | 3/1991 |
| DE | 19841615 | 3/2000 |
| DE | 19939350 * | 2/2001 |
| EP | 0229022 | 7/1987 |
| EP | 0606599 A1 | 7/1994 |
| EP | 0681029 A2 | 11/1995 |
| EP | 1481671 | 12/2004 |
| EP | 1543834 | 6/2005 |
| EP | 1 938 828 | 7/2008 |
| GB | 2330076 | 4/1999 |
| JP | 52145509 | 12/1977 |
| JP | 58009084 | 2/1983 |
| JP | 59059623 | 4/1984 |
| JP | 63211219 | 9/1988 |
| JP | 363211219 | 9/1988 |
| JP | 04202138 | 7/1992 |
| JP | 4202138 | 7/1992 |
| JP | 6312924 | 11/1994 |
| JP | 07165583 | 6/1995 |
| JP | 07194351 | 8/1995 |
| JP | 8073369 | 3/1996 |
| JP | 08073369 | 3/1996 |
| JP | 9067245 | 3/1997 |
| JP | 409067245 | 3/1997 |
| JP | 10025247 | 1/1998 |
| JP | 410025247 | 1/1998 |
| JP | 10152428 | 6/1998 |
| JP | 10179129 | 7/1998 |
| JP | 11246399 | 9/1999 |
| JP | 11513037 | 11/1999 |
| JP | 11335231 | 12/1999 |
| JP | 2001161338 | 6/2001 |
| JP | 2002-12550 | 1/2002 |
| JP | 2002-505296 | 2/2002 |
| RU | 2045955 | 10/1995 |
| SU | 1247011 | 7/1986 |
| WO | WO 9507079 | 3/1995 |
| WO | 09502202 | 3/1997 |
| WO | WO 97/31630 | 9/1997 |
| WO | WO 9749405 | 12/1997 |
| WO | WO 99/44623 | 9/1999 |
| WO | WO99/44623 | 9/1999 |
| WO | WO 99/61038 | 12/1999 |
| WO | WO 00/68356 | 11/2000 |
| WO | WO 00/74696 | 12/2000 |
| WO | WO00/74696 | 12/2000 |
| WO | WO02/02582 | 1/2002 |
| WO | WO 02/02582 | 1/2002 |
| WO | WO 02/32234 | 4/2002 |
| WO | WO 03/000185 | 1/2003 |
| WO | WO 03/035007 | 5/2003 |
| WO | WO 03/068205 | 8/2003 |
| WO | WO 03/075943 | 9/2003 |
| WO | WO 03/082249 | 10/2003 |
| WO | WO 2004/037180 | 5/2004 |
| WO | WO 2004/062611 | 7/2004 |
| WO | WO 2005/084230 | 9/2005 |
| WO | WO 2006/053249 | 5/2006 |
| WO | WO 2006/062681 | 6/2006 |
| WO | WO 2007/067812 | 6/2007 |
| ZA | 200000857 | 8/2001 |

OTHER PUBLICATIONS

Brown, et al. J. Chem. Soc. 545 (1959).
Byrne, et al. J. Chem. Soc. (c):2810 (1971).
Carroccio, et al. Clin. Chem. 49:861-867 (2003).
Carson, j. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chou et al. Eur. J. Biochem. 115:207-216 (1981).
Chou, et al. Adv enzyme regul 22:27-55 (1984).
Chou, et al. J. Biol. Chem. 252:6438-6442 (1977).
Chou, et al, J. Theor. Biol. 35:285-297 (1972).
Chou, et al. Trends Pharm. Sci. 4:450-454 (1983).
Chou, j. Theor. Biol. 59:253-276 (1976).
Costa, et al. Digest. Liver Dis. 35:642-647 (2003).
Davis, WL. Abstract—Fertiliser, Feeding stuffs and Farm Supplies J. 11:694 (1926).
Ding, et al. Biochem. Biophy. Res. Comm. 261:218-223 (1999).
Friedman, et al. J Cutan Med. Surg. 6(5):449-459 (2002).
Germany, "The Absolutely German Drink," contents of beer, 2004, 5 pages.
Goldstein, et al. Am. J. Gastroenterol. 96:1019-1027 (2001).
Halter, et al. Gut 49:443-453 (2001).
Hamber, et al. J. Bio. Chem. 246:6713-6721 (1971).

Huang, et al. Cancer Res. 51:813-819 (1991).
International Search Report for PCT/US02/19617.
International Search Report for PCT/US04/16043.
Jach, Przegl Dermatol. 65(4):379-382 (1978).
Kanematsu, et al. J Bone Miner Res 12(11):1789-1796 (1997).
Lopes, Curr. Med Res Opin. 8:145-149 (1982).
Meling, et al. Scand. J. Gastroenterol. 31:339-344 (1996).
Noreen, et al. J. Nat. Prod 61:2-7 (1998).
Pairet, et al. Inflamm. Res 47, Supplement 2s93-s101 (1998).
Panglisch, monaffsschrift fuer brauwissen schaft, 1990, 43(1), 4-16.
Pippa, et al. Scand. J. Gastroenterol. Suppl. 167:32-35 (1989).
Plewig, et al. J. Invest. Dermatol. 65(6):532-536 (1975).
Poullos, et al. J. Gastroenterol. Hepatol. 18:756-762 (2003).
Ringbom, et al. J. Nat Prod 61:1212-1215 (1998).
Røseth, digest. Liver Dis. 35:607-609 (2003).
Schjerven, et al. Br. J. Dermatol. 149:484-491 (2003).
Shah, et al. Gut 48:339-346 (2001).
Shimamura, et al. Biochem. Biophys. Res. Comm. 289:220-224 (2001).
Shureiqi, et al. Cancer res. 61:6307-6312 (2001).
Sivri, fundam. Clinic. Pharmacol. 18:23-31 (2004).
Subbaramaiah, et al. Cancer Res. 60:2399-2404 (2000).
Suh, et al. Cancer Res. 58:717-723 (1988).
Tagashira, et al., Biosci. Biotech. Biochem. 59(4):740-742 (1996).
Thomas m. Newmark and paul schulick, Beyond Aspirin nature's answer to arthritis, cancer & alzheimer's disease, hohm press (2000) release 7; pp. 147-151, 248.
Tibble, et al. Drugs Today 37:85-96 (2001).
Tibble, et al. Gut 45:362-366 (1999).
Tobe, et al. Biosci. Biotech. Biochem 61(1):158-159 (1997).
Wang, et al. Free Radical Biology & Medicine 27:612-616 (1999).
Warner, et al. Proc Natl Acad Sci USA 96:7563-7568 (1999).
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26:753-760 (2003).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids: Elsevier, Chapters 6, 8 pages (1991).
Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography A 1192(1):191-3 (May 23, 2008) (Epub Apr. 8, 2008); abstract only (1 page).
Bermejo, et al. Rev. Esp. Enferm. Dig. 95(9): 621-624 and 625-628 (2003).
Bolick D et al., Endocrinology 144(12), pp. 5227-5231 (Dec. 2003).
Carroccio, et al. Clin. Chem. 49(6):861-867 (2003).
Chandra, et al., "Anti-inflammatory and Anti-Arthritic Activity of Volatile Oil of Curcuma Longa (Haldi)", Indian Journal of Med. Research, vol. 60, No. 1, 1972, 138-142.
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou, et al. Adv enzyme regul 22:27-55 (1983).
Chou, et al. Eur. J. Biochem. 115:207-216 (1981).
Chou, et al. J. Biol. Chem. 252(18):6438-6442 (1977).
Chou, et al., TIPS, pp. 450-454, Nov. 1983.
Cohen, Protein Kinases—the major drug targets of the twenty-first century? Nature Reviews, 1: 309-315 (2002).
Davies, WL. Abstract—Fertiliser, Feeding Stuffs and Farm Supplies J. 11:694 (1926).
De Keukeleire "Fundamentals of Beer and Hop Chemistry" Quimica Nova, 23(1) pp. 108-112 (2000).
EP Search Report for EP App. No. 07809709.4.
European Search Report EP 05 723 839.6.
European Search Report for corresponding EP Application No. 02737562.5 (4 pages).
European Search Report for related European Application No. 02784313.5.
Exercise as Treatment for Arthritis, Rheumatic and Immunologic Diseases, Cleveland Clinic, www.clevelandclinic.org, Mar. 14, 2000.
Extended European Search Report EP 10162893.1.
Extended European Search Report EP 07717798.8.
Extended European Search Report EP 07809708.6.
Foucault et al., J. Chromatography A 808(1-2):3-22 (May 29, 1998); abstract only (3 pages).
Gao et al., J. Food Sci. Nutr. vol. 9, pp. 240-244 (2004).
Gerhauser, Beer Constituents as Potential Cancer Chemopreventive Agents, EP Journal of Cancer 41; 1941-1954: (2005).
Gilani, "Studies on Antihypertensive and Antispasmodic Activities of Methanol Extract of Acacia nilotica Pods", Phytotherapy Research 13: 665-669 (1999).
Goldstein, et al. Am. J. Gastroenterol. 96(4):1019-1027 (2001).
Hamberg, et al. J. Bio. Chem. 246(22):6713-6721 (1971).
Information on ArthroTrimTM product', downloaded from Internet Aug. 30, 2002.
Information on "Hops and Beer Flavours", IOB Technical Symposium, Apr. 2001, pp. 1-9.
Information on "Zyflamend and Zyflamend PM", downloaded from Internet Aug. 30, 2002.
International Search Report for Corresponding PCT Application No. PCT/US05/41018; 2pp.
International Search Report for PCT /US06/30920, Aug. 3, 2007, 3 pages.
International Search Report for PCT/US06/47196.
Jach, Przegl Dermatol. 65(4):379-381 (1978).
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to Kaltner, D., Technische Universitat Munchen, (Nov. 30, 2000), pp. 1-193, plus Tabs. AH1-A.
Konda, et al., Arthritis & Rheumatism 62(6): 1683-1692, (2010).
Lamy Virginie et al., Apoptosis, an Int'l Journal on Programmed Cell Death,13(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. Of American Soc. For Experimental Biol., vol. 18, No. 4-5 (Jan. 1, 2004).
Lopes, Curr. Med Res Opin. 8(3):145-149 (1982).
Mannering et al., Food, Nutrition and Chemical Toxicity X(X), pp. 311-323 (Jan. 1, 1993).
Minich et al., Journal of nutrition and Metabolism, vol. 2010, article ID 467316, pp. 1-11, (2010).
Newark, et al., "Beyond Aspirin", pp. 147-151, Hohm Press (2000).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/649,584 on Mar. 3, 2010.
Office Action issued in U.S. Appl. No. 11/344,552 on Sep. 8, 2010.

Office Action issued in U.S. Appl. No. 11/501,393 on Aug. 25, 2010.
Office Action issued in U.S. Appl. No. 12/030,335 on Oct. 21, 2010.
Office Action issued in U.S. Appl. No. 11/636,867 on Aug. 30, 2010.
Office Action issued in U.S. Appl. No. 11/729,696 on Mar. 25, 2010.
Pairet, et al. Inflamm. Res 47(2), s93-s101 (1998).
Panglisch, Monafsschrift fuer Brauwissen Schaft, 43(1), 4-16 (1990).
Parts per Milliion, 1 page, 2004.
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.
Rahman, M.M., et al., "Conjugated linoleic acid inhibits osteoclast differentiation of RAW264.7 cells by modulating RANKL signaling" J. Lipid Res., 47(8): 1739-1748, (2006).
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Suh, et al. Cancer Res 58:717-723 (1988).
Supplemental European Search Report for EP 07845228.
Supplementary European Search Report from related EP Application No. 05851567, 8PP.
Supplementary Partial European Search Report for related European Patent Application No. 05723895.8, 5 pages (2007).
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Ward, et al., Therapeutic Potential of Phosphoinositide 3-Kinase Inhibitors, Chemistry & Biology, vol. 10, 207-210, Mar. 2003.
Written Opinion for corresponding PCT Application No. PCT/US05/41018; 3 pp.
Yui, et al. Biol. Pharm. Bull. 26(6):753-760 (2003).
Zhao Feng et al., Biological and Pharmaceutical Bulletin, 26(1), pp. 61-65 (Jan. 2003).
Exercise as Treatment for Arthritis, Rheumatic and Immunologic Diseases, Cleveland Clinic, www.clevelandclinic.org, 2007.
Kaltner, D., Untersuchungen zur Ausbildung des Hopfenaromas and technologische MaBnahmen zur Erzeugung hopfenaromatischer Biere, Technische Universitat Munchen, (Nov. 30, 2000), pp. 1-193, plus Tabs. AH1-AH31.
Provital Group, Rosemary-eco Botany. 2007 (9 pages).
Smith, et al., Natural Foam Stabilizing and Bittering Compounds Derived From Hops, Journal of the American Society of Brewing Chemists, vol. 56, No. 2, 1998, pp. 52-57.
Vanhoenacker, et al., Analysis of iso-alpha-acids and reduced iso-alpha-acids in beer by direct injection and liquid chromatography with ultraviolet absorbance detection or with mass spectrometry, Journal of Chromatography, vol. 1035, No. 1, (Apr. 30, 2004), pp. 53-61.
Supplementary Partial European Search Report for related European Patent Application No. 05723895.8, dated Apr. 20, 2007, (5 pages) (cited references are enclosed, see C59, C61-C62).
English Translation of cover page, pp. 1-2, tables on pp. 30, 78, 122, and p. 142 of reference C59 (Kaltner, D., Untersuchungen zur Ausbildung des Hopfenaromas und technologische MaBnahmen zur Erzeugung hopfenaromatischer Biere, Technische Universitat Munchen, (Nov. 30, 2000), pp. 1-193, plus Tabs. AH1-AH31.) filed on Sep. 17, 2007. See also Reference C63 regarding same.

* cited by examiner

INHIBITION OF COX-2 AND/OR 5-LOX ACTIVITY BY FRACTIONS ISOLATED OR DERIVED FROM HOPS

CROSS-REFERENCE TO RELATED APPLICATIONS

This patent application is a continuation-in-part of U.S. application Ser. No. 10/689,856, filed Oct. 20, 2003, now U.S. Pat. No. 7,270,835, which is a continuation-in-part of U.S. application Ser. No. 10/464,410, filed Jun. 18, 2003, which is a continuation-in-part of U.S. application Ser. No. 10/400,293, filed Mar. 26, 2003 (abandoned), and a continuation-in-part of U.S. application Ser. No. 10/401,283, filed Mar. 26, 2003 (abandoned), both of which claim the benefit under 35 U.S.C. §119(e) to provisional application No. 60/450,237, filed on Feb. 25, 2003, and provisional application No. 60/420,383, filed on Oct. 21, 2002; and is a continuation-in-part of U.S. patent application Ser. No. 10/464,834, filed Jun. 18, 2003, which is a continuation-in-part of U.S. application Ser. No. 10/400,293, filed Mar. 26, 2003 (abandoned), and a continuation-in-part of U.S. application Ser. No. 10/401,283, filed Mar. 26, 2003 (abandoned), both of which claim the benefit under 35 U.S.C. §119(e) to provisional application No. 60/450,237, filed on Feb. 25, 2003, and provisional application No. 60/420,383, filed on Oct. 21, 2002. This application is also a continuation-in-part of U.S. application Ser. No. 09/885,721, filed Jun. 20, 2001, now U.S. Pat. No. 7,205,151. The contents of each of these earlier applications are hereby incorporated by reference as if recited herein in their entirety.

BACKGROUND OF THE INVENTION

This invention primarily relates to the method and use of fractions isolated or derived from hops as inhibitors of COX-2 and/or 5-LOX activity, particularly reduced isoalpha acids (RIAA), isoalpha acids (IAA), tetrahydroisoalpha acids (THIAA), hexahydroisoalpha acids (HHIAA), alpha acids, beta acids, spent hops, and hop essential oils.

Thrombosis—the current most common cause of ischaemic cardiovascular disease (CVD) such as myocardial infarction and stroke—is the late complication of atherosclerosis, a progressive inflammatory disease characterized by lipid infiltration in the wall of large arteries (atherosclerotic plaques). Platelet and leukocyte recruitment on endothelial cells constitutes an early mechanism of vascular inflammatory damage and consequent vessel occlusion. The increasing appreciation of the role of inflammation in atherosclerosis and thrombosis has renewed interest in the possibility that anti-inflammatory compounds might be effective in the prevention of CVD. Such an intriguing possibility was first raised when acetylsalicylic acid (aspirin) was shown to reduce platelet aggregation induced by several physiological stimuli. Because platelet aggregation was known to play a crucial role in thrombosis, it was anticipated that the newly described anti-aggregating activity of aspirin (at that time, a 70-year-old anti-inflammatory drug) might translate to a clinical benefit in CVD. Aspirin was then tested in dozens of clinical trials and was shown to reduce, by approximately 25%, both primary and secondary incidence of myocardial infarction and other CVDs. However, the gastric side-effects (mainly haemorrhagic) associated with aspirin limited its widespread clinical use for the prevention of cardiovascular events.

The anti-thrombotic effect of aspirin had been related to the inhibition of the platelet enzyme cyclooxygenase (COX), which catalyses the first step in the formation of thromboxane A2 ($TxA_2$), an arachidonic-acid-derived prostanoid that initiates platelet aggregation. Because inhibition of COX in the gastric mucosa would also prevent the formation of cytoprotective prostaglandins, the beneficial anti-platelet effect of aspirin appeared to be inseparable from its gastric side-effects. Following the discovery of a second isoform of the COX enzyme in leukocytes and inflamed tissues, the constitutive enzyme, already described in platelets and endothelial cells, was named COX-1 to distinguish it from the inducible, comparatively aspirin-insensitive COX-2.

Among several alternatives to aspirin, such as the use of drugs that inhibit platelet function without affecting COX-1 activity, two relatively newer antithrombotic approaches will be discussed, both of which are based on the modulation of arachidonic acid metabolism in cells other than platelets, such as blood leukocytes. The first approach focuses on the development of selective drugs that inhibit the production of inflammatory prostaglandins catalyzed by COX-2. This approach leaves COX-1-dependent gastric mucosal function intact but does not prevent platelet activation. Although variable and transient expression of COX-2 has been reported recently in platelets in different clinical settings, it is unlikely that COX-2 inhibitors would affect $TxA_2$-dependent platelet function. The second approach considers 5-lipoxygenase (5-LOX), an enzyme that catalyses the formation of leukotrienes (LTs), as a novel potential target to reduce the atherogenic and thrombogenic role of leukocytes and platelets and their interaction.

Forty years ago, activated platelets were shown to produce inflammatory prostaglandins ($PGE_2$ and $PGF_{2\alpha}$), a reaction prevented by aspirin and other non-steroidal anti-inflammatory drugs (NSAIDs). In the following few years, arachidonic acid, the 20-carbon-atom fatty acid precursor of prostaglandins, was identified as an initiator of platelet aggregation following its rapid metabolism to intermediate prostaglandin endoperoxides and $TxA_2$, the labile end-products in platelets. The long-lasting (several days) activity of aspirin was attributed to its acetyl group, which was indeed able to irreversibly inactivate COX-1, the platelet enzyme that catalyses the first steps of the arachidonic acid metabolism cascade.

Prostacyclin ($PGI_2$), another metabolite of arachidonic acid produced by the action of COX-1, has been identified in endothelial cells. Because $PGI_2$, in contrast to $TxA_2$, inhibits platelet aggregation, doubts were raised about the clinical potential of aspirin as an anti-thrombotic drug. The assumption was made that to achieve full anti-thrombotic efficacy, the inhibitory effect of aspirin on platelet COX-1 should be retained while that on vascular COX-1 should be minimized (the so-called 'aspirin dilemma'). Low-dose aspirin (75-100 mg, daily, p.o., in healthy volunteers), which is virtually devoid of a measurable anti-inflammatory effect, was shown to abolish platelet $TxA_2$ generation while leaving vascular $PGI_2$ formation almost intact. However, the epidemiological observation that any dose of aspirin tested (between 30 and 1500 mg, daily, including the highest doses that inhibit both $TxA_2$ and $PGI_2$ generation) was equally effective as an anti-thrombotic, led many researchers to believe that inhibition of platelet COX-1 was indeed the crucial target of aspirin, with concomitant vascular COX-1 suppression having minor, if any, clinical relevance.

Prostaglandins formed by inducible COX-2, including $PGI_2$ in endothelial cells, mediate the development of classical signs of inflammation, such as leukocyte activation, vasodilatation, pain and edema. Although recent work has shown that both COX-1 and COX-2 expression is increased in response to inflammatory stimuli and COX-2 is constitutive in several tissues, the differences between the two COX isoenzymes have led to the development of new concepts in inflammation and its control.

COX-2 is expressed largely in circulating blood leukocytes, vascular cells and macrophages that infiltrate atherosclerotic plaques. This is consistent with a possible direct contribution of leukocytes to vascular disease and thrombus formation. A possible platelet-mediated thrombogenic role of blood leukocytes is also attracting much attention. Activated platelets can recruit leukocytes at the site of vascular injury and form stable conjugates through an adhesion cascade between platelet P-selectin and the leukocyte β2 integrin Mac-1; conversely, activated leukocytes release substances that activate platelets and degrade the endothelial barrier function. Activated platelets can substitute for endothelial cells in the recruitment and migration of leukocytes through the damaged vessel, and leukocytes can accumulate in a growing thrombus and contribute to further platelet activation and deposition and the initiation of blood clotting.

Activated leukocytes, platelet-neutrophil or platelet-monocyte conjugates have been observed in the peripheral blood of patients with unstable angina. In this clinical condition, the presence of platelet-neutrophil conjugates following coronary angioplasty is a predictive index of acute re-occlusion, whereas in acute myocardial infarction the presence of circulating platelet-monocyte aggregates is a sensitive marker of in vivo platelet activation.

Thus, the intriguing possibility is emerging that at the site of an unstable atherosclerotic plaque platelets might be the initial or amplifying trigger of a localized leukocyte-dependent inflammatory response. This is supported by in vivo studies showing co-localization of platelets and leukocytes within atherosclerotic lesions or in areas of ischaemia-reperfusion injury, and activation of neutrophils across the coronary vascular bed in patients with unstable angina, but not in those with stable angina. Activation of neutrophils might be either a marker or a cause (or both) of a widespread inflammatory process occurring in the coronary vasculature. Depending on the intensity of the inflammatory stimuli, such a process might lead to vasoconstriction and thrombosis.

Formation of platelet-leukocyte aggregates within regions of injured vasculature is accompanied by chemokine synthesis in monocytes and the induction of a respiratory burst in neutrophils. If these new perspectives in the pathophysiology of vascular inflammation and thrombosis are confirmed, the use of COX-2 inhibitors to downregulate leukocyte function and their interaction with platelets should be considered. Indeed, aspirin failed, at least in vitro, to modulate platelet-leukocyte interactions.

Selective COX-2 inhibitors might slow down the progression of atherosclerosis and enhance plaque stability, with a possible decrease in atherothrombotic complications. Low-density lipoprotein (LDL)-receptor-deficient mice, fed a lipid-enriched atherosclerotic diet, develop early atherosclerotic lesions in which COX-2 expression can be detected. In this model, either selective inhibition of COX-2 by rofecoxib or suppression of the gene encoding COX-2 resulted in the prevention of atherosclerotic lesion formation without any modification of serum lipids. Furthermore, in a mouse model of acute myocardial infarction, rofecoxib reduced macrophage infiltration. More recently, celecoxib, another COX-2 inhibitor, was shown to improve endothelial function in patients with coronary artery disease.

Together, these data suggest that COX-2 inhibitors might reduce the inflammatory contribution to vascular damage and atherothrombosis, and have the potential advantage over aspirin of minimal gastric side-effects. Furthermore, an intact platelet function in the presence of COX-2 inhibitors might reduce bleeding complications, which are associated with aspirin treatment. COX-2 inhibition would be particularly beneficial in those patients with arthritis or other chronic inflammatory diseases, who have additional cardiovascular risk.

Unlike COX-2, which is expressed in different cell types, including leukocytes and endothelial cells, another enzyme that catalyses arachidonic acid metabolism, 5-lipoxygenase (5-LOX), is only expressed in a limited number of cells (mostly leukocytes). The metabolic products of arachidonic acid that result from the catalytic activity of 5-LOX are the leukotrienes (LTs), which possess potent pro-inflammatory activities and thus might be involved in CVD. Indeed, some LTs are potent vasoconstrictors and increase coronary vascular resistance. A decrease in the production of LTs in leukocytes by 5-LOX inhibitors might achieve downregulation of leukocyte function without undesired effects on other cells, such as endothelial cells. In this way, the balance between the beneficial and detrimental effects of COX-2 inhibitors possibly linked to the concomitant reduction of pro-inflammatory and anti-inflammatory prostanoids in leukocytes and endothelial cells, respectively, could be overcome.

The transfer of the unstable $LTA_4$ (formed by 5-LOX) from neutrophils to cells that possess $LTC_4$ synthase activity, such as platelets and endothelial cells, gives rise to a process of arachidonic acid transcellular metabolism leading to $LTC_4$ generation. Increased levels of $LTC_4$ have been described in plasma from patients with cerebral infarction, whereas increased urinary excretion of $LTE_4$, a metabolite of $LTC_4$, has been reported following episodes of unstable angina and acute myocardial infarction.

Although the role of neutrophils in inflammation has been linked mainly to the formation of $LTB_4$ (a compound with potent chemo-attractant activities), $LTA_4$ might represent the main metabolite released by neutrophils following 5-LOX activation. Formation of cysteinyl-LTs by cell-cell interaction would then cause coronary vasoconstriction. Thus, inhibition of neutrophil function could not only suppress the direct contribution of these cells to inflammation, but also downregulate the contribution of platelets and other interacting cells.

Cysteinyl-LTs are also thought to be involved in damage to gastric mucosa, a finding that is consistent with some experimental evidence that leukocyte-endothelial cell interaction is a prerequisite for aspirin-induced gastropathy. A reduction in NSAID-induced gastric damage was found in neutropenic rats or by treatment of rabbits with monoclonal antibodies against leukocyte adhesive molecules. In addition, decreased synthesis of cysteinyl-LTs was found in a model of neutrophil-perfused rabbit heart by the use of the monoclonal anti-CD18 antibody. Thus, aspirin might induce the expression of adhesion molecules, such as intercellular cell adhesion molecule 1 (ICAM-1) and P-selectin, on gastric endothelium, which results in leukocyte recruitment and cysteinyl-LT biosynthesis, followed by gastric inflammation and bleeding. The latter consequences could be prevented by inhibition of 5-LOX. However, the precise mechanism(s) underlying this suggestive, but still unproven, sequence of events remain to be elucidated.

Together, the data discussed above suggest that a promising pharmacological approach to reduce cardiovascular events at least as effectively as aspirin but without its gastric side-effects should include the following effects: (1) inhibition of COX-1 to prevent platelet $TxA_2$ formation; (2) inhibition of COX-2 to downregulate leukocyte activation and widespread vascular inflammation; and (3) inhibition of 5-LOX to further, and specifically, reduce leukocyte inflammatory and thrombogenic potential, and to counteract the gastric damage associated with the inhibition of COX-1.

Compounds that are capable of inhibiting both COX and 5-LOX are being developed as anti-inflammatory agents. Further development of some dual inhibitors, including tepoxalin, tebufelone and CI986, has been limited by drug metabolism issues; other dual inhibitors have been shown to have anti-platelet, anti-leukocyte and anti-inflammatory properties together with an improved gastric tolerability.

In particular, licofelone is an effective inhibitor of both $TxA_2$-mediated platelet function and neutrophil activation, the latter measured as LTB4 formation, generation of reactive oxygen species, elastase release and homotypic aggregation induced by different inflammatory stimuli. Licofelone was also able to reduce neutrophil surface expression of Mac-1 and the consequent platelet-neutrophil conjugate formation and transcellular synthesis of $LTC_4$.

In the prevention of atherothrombotic events, licofelone and similar drugs might therefore be at least as effective as low-dose aspirin, without the gastric side-effects of the latter or the pro-thrombotic risk associated with selective COX-2 inhibitors. These drugs might even exert a more powerful anti-thrombotic effect than aspirin through additional anti-inflammatory mechanisms by inhibiting, for example, the availability of intravascular tissue factor from monocytes or endothelial cells exposed to inflammatory agonists, or to prevent tissue factor transfer from leukocytes to platelets. The potential downregulation of blood clotting by dual inhibitors, however, remains to be defined and is the subject of active investigation. In this context, recent reports that NO-aspirin (NCX4016) reduces 5-LOX activity and blunts monocyte tissue factor expression are of interest.

A promising anti-thrombotic approach to minimize the gastric side-effects of aspirin and the cardiovascular risk of COX-2 inhibitors is to concurrently depress the activities of both COX and 5-LOX enzymes. Several such dual inhibitors of the production of PGs and LTs in vitro have been identified. Some of these inhibitors, such as licofelone, are presently being evaluated in Phase III clinical studies for the treatment of osteoarthritis. The translation of the promising preclinical and safety profile to the clinical arena awaits the completion of thorough clinical investigations.

Thus, only large-scale randomized controlled clinical trials will show whether, while representing a better and/or safer tool for the treatment of inflammatory disorders, these new drugs can also antagonize interactions between blood and vascular cells that promote inflammatory events, such as atherothrombosis, thus reducing the risk of clinical cardiovascular outcomes.

5-LOX has also been implicated in the progression of certain cancers. For example, see Ding, et. al., *Biochem. Biophy. Res. Comm.*, 261, 218-223 (1999) and Shureiqi, et. al., *Cancer Res.*, 61, 6307-6312 (2001). For a detailed discussion of the advantages of dual COX-2/5-LOX inhibitors see, for example, Charlier, et. al., *Eur. J. Med. Chem.*, 38, 645-659 (2003).

We have surprisingly discovered that fractions derived or isolated from hops have utility in treating the myriad of diseases associated with hyperactivity of COX-2 and/or 5-LOX.

SUMMARY OF THE INVENTION

The invention provides a method of treating or inhibiting a pathological condition in a mammal involving inhibiting inducibility or activity of cyclooxygenase-2 (COX-2) and/or 5-lipoxygenase (5-LOX), the method comprising administering to the mammal a composition comprising a fraction isolated or derived from hops. The fraction isolated or derived from hops may be selected from the group consisting of alpha acids, isoalpha acids, reduced isoalpha acids, tetra-hydroisoalpha acids, hexa-hydroisoalpha acids, beta acids, hop essential oils, and spent hops.

The early mechanisms leading to pathological conditions, or the pathological conditions themselves, which may be treated by the compositions of the present invention include, for example, allergic disorders, cancers (e.g., breast cancer, prostate cancer, colon cancer, pancreatic cancer), inflammatory diseases (e.g., asthma, Alzheimer Disease, arthritis, Crohn's Disease, eczema, Inflammatory Bowel Disease, osteoarthritis, psoriasis), gastroprotection via 5-LOX inhibition, cardiovascular disease via LOX and COX inhibition of atherosclerosis, and inhibition of platelet aggregation.

DETAILED DESCRIPTION OF THE INVENTION

The present invention provides compositions, methods, and uses of fractions isolated or derived from hops to inhibit COX-2 and/or 5-LOX activity.

As used herein, the term "dietary supplement" refers to compositions consumed to affect structural or functional changes in physiology. The term "therapeutic composition" refers to compounds administered to treat or prevent a disease or to ameliorate a sign or symptom associated with a disease.

As used herein, the term "effective amount" means an amount necessary to achieve a selected result. Such an amount can be readily determined without undue experimentation by a person of ordinary skill in the art.

As used herein, the term "substantial" means being largely but not wholly that which is specified.

As used herein, the terms "derivatives" or a matter "derived" refer to a chemical substance related structurally to another substance and theoretically obtainable from it, that is, a substance that can be made from another substance. Derivatives can include compounds obtained via a chemical reaction. Methods of making derivatives of compounds are well known to those skilled in the art.

As used herein, the term "hop extract" refers to the solid material resulting from (1) exposing a hops plant product to a solvent, (2) separating the solvent from the hops plant products, and (3) eliminating the solvent.

As used herein, the term "solvent" refers to a liquid of aqueous or organic nature possessing the necessary characteristics to extract solid material from the hop plant product. Examples of solvents would include, but are not limited to, water, steam, superheated water, methanol, ethanol, hexane, chloroform, methylene chloride, liquid supercritical $CO_2$, liquid $N_2$, or combinations of such materials.

As used herein, the term "$CO_2$ extract" refers to the solid material resulting from exposing a hops plant product to a liquid or supercritical $CO_2$ preparation followed by the removing of the $CO_2$.

As used herein, the term "spent hops" refers to the solid and hydrophilic residue from the extraction of hops.

As used herein, the term "alpha acid" refers to compounds collectively known as humulones and can be isolated from hops plant products including, among others, humulone, cohumulone, adhumulone, hulupone, and isoprehumulone.

As used herein, the term "isoalpha acid" refers to compounds isolated from hops plant products and which subsequently have been isomerized. The isomerization of alpha acids can occur thermally, such as boiling. Examples of isoalpha acids include, but are not limited to, isohumulone, isocohumulone, and isoadhumulone.

As used herein, the term "reduced isoalpha acid" (also sometimes referred to as dihydroisoalpha acids or rho-isoalpha acids) refers to alpha acids isolated from hops plant product and which subsequently have been isomerized and reduced, including cis and trans forms. Examples of reduced isoalpha acids (RIAA) include, but are not limited to, dihydro-isohumulone, dihydro-isocohumulone, and dihydro-isoadhumulone.

As used herein, the term "tetra-hydroisoalpha acid" refers to a certain class of reduced isoalpha acid. Examples of tetra-hydroisoalpha acid (THIAA) include, but are not limited to, tetra-hydro-isohumulone, tetra-hydro-isocohumulone and tetra-hydro-isoadhumulone.

As used herein, the term "hexa-hydroisoalpha acid" refers to a certain class of reduced isoalpha acid. Examples of hexa-hydroisoalpha acids (HHIAA) include, but are not limited to, hexa-hydro-isohumulone, hexa-hydro-isocohumulone and hexa-hydro-isoadhumulone.

As used herein, the term "beta-acid fraction" refers to compounds collectively known as lupulones including, among others, lupulone, colupulone, adlupulone, tetrahydroisohumulone, and hexahydrocolupulone.

As used herein, the term "essential oil fraction" refers to a complex mixture of components including, among others, myrcene, humulene, beta-caryophyleen, undecane-2-on, and 2-methyl-but-3-en-ol.

At its simplest, hop extraction involves milling, pelleting and re-milling the hops to spread the lupulin, passing a solvent through a packed column to collect the resin components and finally, removal of the solvent to yield a whole or "pure" resin extract.

The composition of the various extracts is compared in Table 1.

TABLE 1

Hop extracts (Percent w/w)

| Component | Hops | Organic Solvent | Super Critical $CO_2$ | Liquid $CO_2$ |
|---|---|---|---|---|
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts essentially none of the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (89-93%) is lower than that of supercritical $CO_2$ (91-94%) or the organic solvents (93-96%). Following extraction, there is the process of solvent removal, which for organic solvents involves heating to cause volatilization. Despite this, trace amounts of solvent do remain in the extract. The removal of $CO_2$, however, simply involves a release of pressure to volatize the $CO_2$.

Hop $CO_2$ extracts can be fractionated into components, including hops oils, beta acids, and alpha acids. Hops oils include, but are not limited to, humulene, beta-caryophyllene, mycrene, farnescene, gamma-cadinene, alpha-selinene, and alpha-cadinene. Beta acids include, but are not limited to, lupulone, colupulone, adlupulone, tetrahydroisohumulone, and hexahydrocolupulone, collectively known as lupulones. Beta acids can be isomerized and reduced. Beta acids are reduced to give tetra-beta acids. Alpha acids include, but are not limited to, humulone, cohumulone, adhumulone, hulupone, and isoprehumulone. Alpha acids can be isomerized to give isoalpha acids. Iso-alpha acids can be reduced to give reduced-isoalpha acids, tetra-hydroisoalpha acids, and hexa-hydroisoalpha acids.

Tetrahydroiso-alpha-acids (tetrahydroisohumulones) usually are prepared from the beta-acids (or lupulones) in hop extracts. The hop extracts also contain alpha-acids (or humulones) but they are not normally used to make tetrahydroiso-alpha-acids for economical reasons. Alpha-acids and beta-acids are often referred to as "soft resins". The alpha-acids consist of three major analogs: cohumulone, humulone and adhumulone. Beta-acids consist of three major analogs: colupulone, lupulone and adlupulone. Tetrahydroiso-alpha-acids can be prepared from either alpha-acids or from beta-acids which results in three analogs and two diastereoisomers. They are cis and trans-isomers of tetrahydroiso-cohumulone (THICO), tetrahydroiso-humulone (THISO) and tetrahydroiso-isoadhumulone (THIAD).

Worden, et al., U.S. Pat. No. 3,552,975, teach a method employing organic solvents and lead salts to make tetrahydroiso-alpha-acids from beta-acids. The final product is a crude mixture from which the lead residues can only be removed with great difficulty. The presence of residual lead in products to be consumed is obviously undesirable.

Worden, U.S. Pat. No. 3,923,897, discloses a process for preparing tetrahydroiso-alpha-acids from beta-acids by oxidizing desoxytetrahydro-alpha-acids (resulting from the hydrogenation of beta-acids) with a peracid followed by the isomerization of the resulting tetrahydro-alpha-acids. The process does not utilize lead salts but it is conducted in water immiscible organic solvents and it involves cumbersome solvent changes which increase process cost. The presence of even residual amounts of such solvents in food products, such as beverages, is undesirable.

Cowles, et al., U.S. Pat. No. 4,644,084, disclose a process for making tetrahydroiso-alpha-acids by treating beta-acids to form desoxytetrahydro-alpha-acids which are dissolved in an aqueous alcoholic caustic solution and then oxidized with an oxygen-containing gas to form the desired tetrahydroisoalpha-acids. The Cowles, et al. process does not use undesirable organic solvents and is superior to other known processes using beta-acids.

Hay, U.S. Pat. No. 5,013,571, teaches a process for simultaneously isomerizing and reducing alpha acids to tetrahydroiso-alpha-acids (THIAA). The Hay process uses relatively high pHs (8 to 10), significant amounts of water, high temperature, and hydrogen pressures above about 50 psig. As a result, side reactions can take place that can result in undesired products. Furthermore, the desired tetrahydroiso-alpha-acids are not easily isolated from the Hay reaction mixture.

Hydrogenation and hydrogenolysis are well-known processes which are commonly employed in many organic chemical synthesis schemes, including the manipulation of lupulones and humulones, and their derivatives. Usually, low molecular weight organic compounds are used as solvents ($C_1$-$C_6$). For example, Carson, 73 J. Am. Chem. Soc. 1850-1851 (1951), discusses the hydrogenation of lupulone and humulone using methanol as a solvent. Anteunis, et al., Bull. Soc. Chim. Belg. 476-483 (1959), disclose carrying out the hydrogenation of humulone in methanol or ethanol.

Wilkinson, U.S. Pat. No. 3,933,919, discloses hydrogenation, hydroformylation and carbonylation reactions using methanol, ethanol, and benzene as solvents. The Cowles patent, supra, discloses a process for hydrogenating beta acids to form desoxytetrahydro-alpha-acids where ethanol is used as a solvent. Todd, Jr., et al., U.S. Pat. Nos. 5,082,975 and 5,166,449, disclose the hydrogenation in water/methanol of beta acids to form hexahydro-beta-acids. Stegink, et al., U.S. Pat. No. 5,296,637, teach hydrogenation of alpha acids to form tetrahydro-alpha-acids using an aqueous or aqueous/lower alkanol solvent medium.

For a detailed discussion of the above methods of making various fractions isolated or derived from hops, see U.S. Pat. No. 6,020,019.

In one commercial process, alpha acids are isomerized and reduced to dihydroisoalpha acids under basic conditions with a reducing agent such as sodium borohydride at elevated temperatures. In another commercial process, alpha acids are isomerized into isoalpha acids under basic conditions at elevated temperatures. Tetrahydroisoalpha acids are produced commercially by a multi-step route from beta acids, and hexahydroisoalpha acids are produced commercially by a reduction of tetrahydroisoalpha acids.

In addition, the literature teaches the hydrogenation of normal homolog isoalpha acids at a pH of about 3 resulting in low yields of tetrahydroisoalpha acid (P. M. Brown, G. A. Howard and A. B. Tatchell, J. Chem. Soc. 545 (1959)). That reference also teaches the hydrogenation with platinum oxide of normal homolog isoalpha acids at a pH of about 10 to give a low yield of isoalpha acids with only one double bond hydrogenated. The reference also teaches the hydrogenation of normal homolog isoalpha acids at a pH of about 3 to yield a deoxygenated THIAA. Another reference teaches the reduction of THIAA to deoxygenated products by hydrogenation with palladium on carbon in methanol at a pH of about 3 (E. Byrne and S. J. Shaw, J. Chem. Soc. (C), 2810 (1971)).

For detailed discussions of methods for making various fractions isolated or derived from hops, see U.S. Pat. Nos. 5,013,571 and 6,583,322.

The invention provides compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Fractions isolated or derived from hops, include, but are not limited to, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters.

Compounds of the fractions isolated or derived from hops can be represented by a supragenus below:

(Supragenus), wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment, compounds of the fractions isolated or derived from hops can be represented by a genus below:

(Genus A), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus A structures include isoalpha acids such as isohumulone, isocohumulone, isoadhumulone, and the like, and reduced isoalpha acids such as dihydro-isohumulone, dihydro-isocohumulone, dihydro-isoadhumulone, and ether or ester conjugates or halogenated modifications of the double bond.

In yet another embodiment, compounds of the fractions isolated or derived from hops can be represented by a genus below:

(Genus B), wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$. Exemplary Genus B structures include tetra-hydroisoalpha acids such as tetra-hydro-isohumulone, tetra-hydro-isocohymulone and tetra-hydro-isoadhumulone, and the like, and hexa-hydroisoalpha acids such as hexa-hydro-isohumulone, hexa-hydro-isocohumulone and hexa-hydro-isoadhumulone, and ether or ester conjugates.

Examples of compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The preferred compounds can bear substituents, as shown in the formula above.

Hops derivatives are known compounds occurring naturally in plants and found in food products and beverages. They may be prepared by any of the extraction and processing methods known in the art. Hops derivatives can be prepared directly from plant material in any known manner. The hops derivatives may be purified by methods known in the art, for example, by recrystallization from aqueous organic solvents such as aqueous alcohols. Synthetic modifications of hops derivatives may be prepared according to methods known in the pharmaceutical art of drug modification.

Further in accordance with the present invention there are provided pharmaceutical formulations of oral dosage forms comprising an effective amount of hops derivatives for release of the active ingredient at a desired site in the gastrointestinal tract, for instance either in the stomach and/or duodenum according to known formulation techniques, for example, rapid- or slow-releasing tablets. Still further in accordance with the invention, there are provided pharmaceutical compositions comprising an effective tolerated amount of hops derivatives. Due to its low toxicity, high dosages of hops derivatives can be employed to produce useful results, depending upon the particular effect that is desired.

Hops derivatives are particularly suitable for oral administration. Therefore, hops derivatives can be formulated for oral use, namely: tablets, coated tablets, dragees, capsules, powders, granulates and soluble tablets, and liquid forms, for example, suspensions, dispersions or solutions, optionally together with an additional active ingredient.

The invention extends to a method of preparing such pharmaceutical compositions as described herein and compositions when so prepared. The compositions may be manufactured by a method which comprises mixing hops derivatives with a pharmaceutically acceptable carrier or auxiliary, and optionally with an analgesic and/or anti-inflammatory substance and/or another compound(s). Methods for preparing a pharmaceutical composition are well known to those skilled in the art (see, for example, Genarro, ed., Remington's Pharmaceutical Sciences, 18th ed., Mack Publishing Co., Easton, Pa. (1990)).

The selected dosage level will depend upon the activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, for example, two to four separate doses per day. It will be understood, however, that the specific dose level for any particular patient will depend upon a variety of factors including body weight, general health, diet, time and route of administration, combination with other compositions and the severity of the particular condition being treated or prevented.

The invention provides methods that include delivering an effective amount of hops fractions, hops compounds, or hops derivatives alone or in combination with an additional active ingredient, as disclosed herein. For example, a daily dose of compositions of the invention can be formulated to deliver about 0.5 to about 10,000 mg of a hops fraction, for example, alpha acid, isoalpha acid, reduced isoalpha acid, tetra-hydroisoalpha acid, hexa-hydroisoalpha acid, beta acid, spent hops, or other hops fractions, per day. In particular, an effective daily dose of compositions can be formulated to deliver about 50 to about 7500 mg of hops fraction, for example, alpha acids, isoalpha acid, reduced isoalpha acid, tetra-hydroisoalpha acid, hexa-hydroisoalpha acid, beta acid, spent hops, or other hops fractions, per day. For example, an effective daily dose of compositions can be formulated to deliver about 100 mg to about 5000 mg, about 200 mg to about 3000 mg, about 300 mg to about 2000 mg, about 500 to about 1000 mg of hops fraction per day. In one embodiment, the effective daily dose is administered once or twice a day. A certain embodiment provides a composition comprising about 0.5 to about 500 mg of isoalpha acid or reduced isoalpha acid, for example, about 50 to about 300 mg or about 100 to about 200 mg of isoalpha acid or reduced isoalpha acid per day. In another embodiment, the invention provides a composition comprising about 10 to about 3000 mg of reduced isoalpha acid, tetra-hydroisoalpha acid, or hexa-hydroisoalpha acid per day, for example, about 50 to about 2000 mg, about 100 to about 1000 mg, about 200 to about 750 mg, or about 250 to about 500 mg of reduced isoalpha acid, tetra-hydroisoalpha acid, or hexa-hydroisoalpha acid per day. Yet another certain embodiment provides a composition comprising about 50 to about 7500 mg of spent hops per day, for example, about 100 to about 6000 mg, about 200 to about 5000 mg, about 300 to about 3000 mg, about 500 to about 2000 mg, or about 1000 to about 1500 mg of spent hops per day.

A composition of embodiments for topical application can contain about 0.001 to about 10 weight percent, for example, about 0.01 to about 5 weight percent, or about 0.1 to about 1 weight percent, of a hops derivative. Such compositions can produce serum concentrations in the range of about 0.0001 to about 10 µM, for example, about 0.001 to about 5 µM, about 0.01 to 1 µM, or about 0.1 to about 0.5 µM of a fraction isolated or derived from hops or conjugate thereof.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in the present composition is contemplated. In one embodiment, talc and magnesium stearate are included in the present formulation. Other ingredients known to affect the manufacture of this composition as a dietary bar or functional food can include flavorings, sugars, amino-sugars, proteins and/or modified starches, as well as fats and oils.

The dietary supplements, lotions or therapeutic compositions of the present invention can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules of tablets. However, the present compositions may also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, grains, animal fats or proteins. Thus, the present compositions can be formulated into cereals, snack items such as chips, bars, chewable candies or slowly dissolving lozenges.

The present invention contemplates treatment of all types of inflammation-based diseases, both acute and chronic. The present formulation reduces the inflammatory response and thereby promotes healing of, or prevents further damage to, the affected tissue. A pharmaceutically acceptable carrier may also be used in the present compositions and formulations.

According to the present invention, the animal may be a member selected from the group consisting of humans, non-human primates, such as dogs, cats, birds, horses, ruminants or other mammals and animals. The invention is directed primarily to the treatment of human beings.

EXAMPLE 1

Inhibition of 5-Lipoxygenase Activity by Derivatives of Alpha-Acids from Hops (*Humulus lupulus*)

Methods

Test Materials and Reagents—Standardized (see Table 2) aqueous solutions of fractions isolated or derived from hops (*Humulus lupulus*) were obtained from BetaTech (Washington, D.C.). The solutions were diluted into DMSO to contain 1 mg/ml of the reference compounds. If necessary, the sample was clarified by centrifugation at 12000×g for 5 minutes. For testing, serial dilutions were made in DMSO. The Lipoxygenase Inhibitor Screening Assay Kit (LISAK) from Cayman (#760700, Chicago, Ill.) was used to assess the effects of test material on lipoxygenase activity. Included with the kit were soybean 15-lipoxygenase (#60700), and linoleic acid. Potato 5-lipoxygenase (#60401) was purchased from Cayman separately. Positive control compounds included caffeic acid (Cayman #70602), Trolox (Sigma 238813) and Rev 5901 (Sigma R5523); these were of the highest purity commercially available. Boswellin (RM07781) was provided by Metagenics, Inc., Gig Harbor, Wash.).

TABLE 2

Description of hop preparations† tested.

| Preparation | Hop Variety | HPLC Analysis (w/w) | Concentration |
|---|---|---|---|
| Alpha Hop | Galena | 82.1% α-acids, 2.7% β-acids, 3.0% Isomerized α-acids. | 1% (w/v) α-acids |
| Beta Acids | Galena | 9.5-10.5% β-acids, <.2% α-acids | 1% (w/v) β-acids |
| Aromahop OE | Galena + Nugget | 25-30% Oil, ~10% β-acids, <.2% Isohop | |
| Isohop | Galena | 25.3% Isomerized α-acids (IAA) | 1% (w/v) IAA |
| Redihop | Galena | 30% α-acids | 1% (w/v) RIAA |
| Tetrahop Gold[1] | Galena | 8.9% THIAA | 1% (w/v) THIAA |
| Hexahop Gold | Galena | 3.9% THIAA, 4.4% HHIAA | 1% (w/v) HHIAA |

†Obtained from Betatech Hops Products, Washington, DC; IAA = isomerized alpha-acids; THIAA = tetrahydro-isoalpha-acids; HHIAA = hexahydro-isoalpha-acids.

Assay—The 5-lipoxygenase (5-LOX) assay and calculations were performed in accordance with the manufacturer's protocol. Briefly, assay buffer was prepared by diluting the contents of LISAK vial #1 with nine parts of HPLC grade water to yield a final concentration of 0.1M Tris-HCl (pH 7.4). 5-LOX was diluted into assay buffer so that the final reaction rate was approximately 10 nmol min$^{-1}$ mL$^{-1}$.

The substrate solution was prepared adding 25 µL of an ethanolic solution of linoleic acid (LISAK vial#6) to 25 µL of 0.1 M KOH (LISAK vial#7) and diluting with 950 µL of HPLC grade water. The final substrate concentration was 1 mM.

The 5-LOX reaction was initiated by adding 10 mL linoleic acid to a reaction mixture consisting of 90 mL of diluted enzyme (or assay buffer for the reaction blank), 10 mL assay buffer and 10 mL of test inhibitor or DMSO. After 5 minutes at room temperature, the reaction was terminated by the addition of 100 mL of the proprietary LISAK chromagen, prepared by mixing equal amounts of LISAK vials 2 and 3. The absorbance was measured with a 492 nm (8 nm bandwidth) filter in a Victor™ Multilabel Counter equipped with an absorbance package (Perkin Elmer #1420-042, #1420-115; Boston, Mass.). The reaction rate was determined as follows:

$$\Delta A\ min^{-1} = (Abs_{rx} - Abs_{enzyme\ blank})/5\ minutes$$

$$nmol\ min^{-1}\ mL^{-1} = \Delta A\ min^{-1}/9.47\ mM^{-1},$$

where the extinction coefficient has been adjusted for the path length created by a volume of 210 µL in a 0.3 cm microtiter well.

Calculations—To assess the probability that the 5-LOX activity of enzyme plus test material was different from the solvent control enzyme activity, the lower 95% confidence limit was computed for the mean of all solvent control values. This lower limit represented a difference of 7.2 percent from the solvent average. Thus, means of duplicate determinations of 5-LOX enzyme plus test material that demonstrated a reduction of enzyme activity greater than 7.2 percent were considered significantly (p<0.05) different from the solvent controls.

Complete dose-response curves were calculated using CalcuSyn (BIOSOFT, Ferguson, Mo.). A the four concentrations test material or positive control used for this computation were 1, 5, 10 and 50 μg/mL. This statistical package performs multiple drug dose-effect calculations using the Median Effect methods described by T-C Chou and P. Talalay [Chou, T. C. and P. Talalay (1984) Quantitative analysis of dose-effect relationships; the combined effects of multiple drugs or enzyme inhibitors. Adv Enzyme Regul 22: 27-55] and is incorporated herein by reference.

Results

Figure 1:
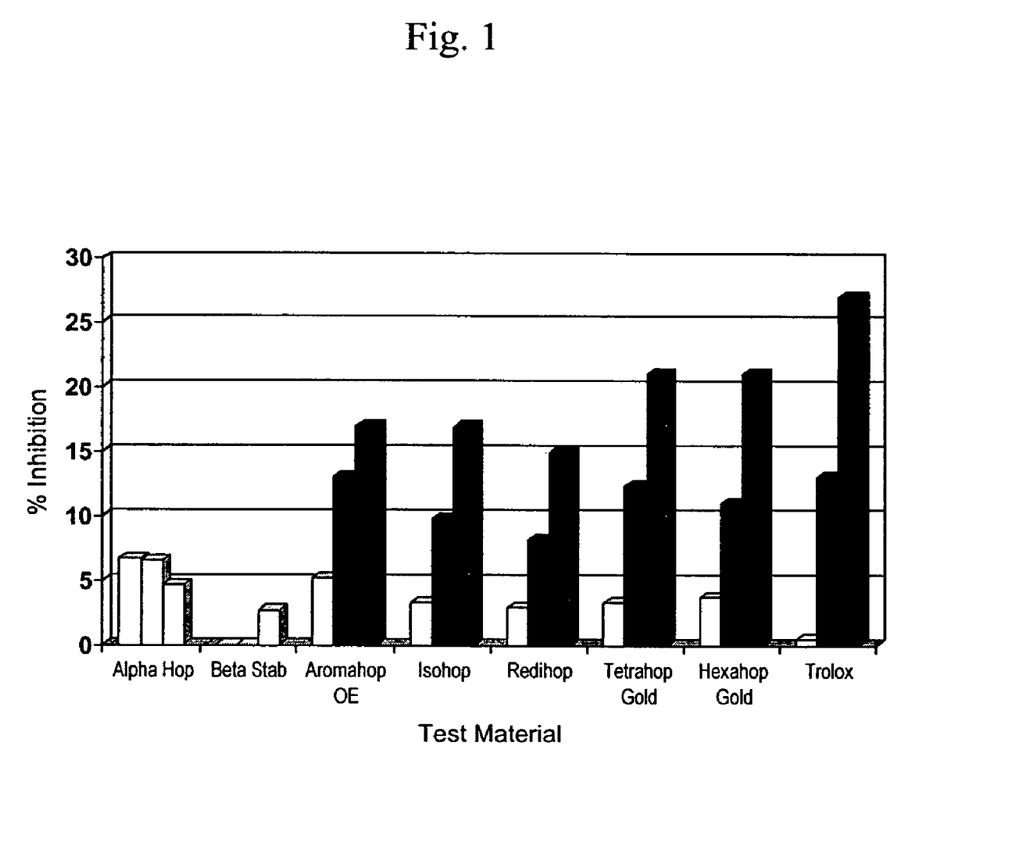
FIG. 1 is a bar graph representing the percent inhibition exhibited by 1, 5, or 10 μg agent/mL for the seven test materials and the Trolox positive control. Each of the three doses is represented by a bar with increasing concentration from left to right. The dark bars indicate those concentrations significantly different from the negative control ($p<0.5$).

We have demonstrated that the chemically modified α-acids from hops inhibit the activity of potato 5-LOX. Unexpectedly, while neither of the native α- or β-acids affected the enzyme until the highest concentration tested, the derivatives of the alpha-acids exhibited significant inhibition at 5 μg/mL, in line with the potent positive control Trolox (Table 3 and FIG. 1). Aromahop OE, an oil fraction of hops, also inhibited 5-LOX at the 5 μg/mL concentration. Tetrahop and Hexahop tended to increase in effectiveness more rapidly than Isohop and Redihop. The hops derivatives were similar in inhibitory activity to Trolox at 5 and 10 μg/mL. However, the synthetic 5-LOX inhibitor was more than twice as active as the natural compounds at the non-physiological 50 μg/mL concentration (data not presented). This finding indicates a steeper dose-response curve for Trolox compared to the hops derivatives. However, at the more physiologically relevant, lower concentrations, the hops derivatives and Trolox expressed similar inhibitory activity of 5-LOX.

A reasonable method of ranking the ingredients is provided in Table 4. The $IC_{25}$s were calculated using the Median Effect Model in CalcuSyn. When ranked in this method Hexahop Gold, Tetrahop Gold, Redihop, Isohop and Aromahop OE were roughly equivalent, $IC_{25}$=18, 17, 24, 29 and 20 μg/mL, respectively, with 95% confidence intervals indicating no differences among the estimate.

TABLE 3

The inhibitory effect of hops-derived compounds on potato 5-lipoxygenase activity at physiologically relevant concentrations†

| | Percent Inhibition | | |
|---|---|---|---|
| Test Material | 1 μg/ml | 5 μg/ml | 10 μg/ml |
| Alpha Hop | 6.7 | 6.5 | 4.7 |
| Beta Stab | 0.0 | 0.0 | 2.7 |
| Aromahop OE | 5.2 | 13‡ | 17 |
| Isohop | 3.3 | 9.8‡ | 17 |
| Redihop | 2.9 | 8.2‡ | 15 |
| Tetrahop Gold | 3.3 | 12‡ | 21 |
| Hexahop Gold | 3.7 | 11‡ | 21 |
| Positive Controls | | | |
| Caffeic acid | 0.0 | 0.0 | 0.0 |
| Boswellin | 2.8 | 2.2 | 2.4 |
| Rev5901 | 2.2 | 0.8 | 0.0 |
| Trolox | 0.5 | 13‡ | 27 |

†Means of duplicate determination relative to control activity of 14 nmol/min/mL, respectively, over the three sets of experiments.
‡The lowest concentration at which inhibition was significantly (p < 0.05) greater than the solvent control; minimum inhibition required for statistical significance (p < 0.05) was 7.2%.

This unanticipated discovery suggests that these derivatives of hops bitter acids will prove to have utility in treating the myriad of diseases associated with hyperactivity of 5-LOX.

TABLE 4

Concentrations of hops compounds and positive controls estimated to inhibit 5-LOX activity by twenty-five percent.

| Test Material | $IC_{25}$† |
|---|---|
| Alphahop | >50 |
| Beta Stab | >50 |
| Aromahop | 20 (10-39) |
| Redihop | 29 (14-61) |
| Isohop | 24 (17-33) |
| Tetrahop | 17 (12-22) |
| Hexahop | 18 (15-23) |
| Positive Controls | |
| Caffeic acid | >50 |
| Boswellin | >50 |
| Trolox | 4.2 (2.6-6.9) |

†values presented as μg/mL; parenthetic values are 95% confidence intervals.

EXAMPLE 2

Antioxidant Activity of Hops Fractions

Methods

Chemicals and reagents—Bacterial lipopolysaccharide (LPS; B E. coli 055:B5) was from Sigma (St. Louis, Mo.). 6-Carboxy-2',7'-dichlorofluorescin diacetate (DCFH-DA) was purchased from Molecular Probes Inc. (Eugene, Oreg.); DCFH-DA was dissolved in dimethyl sulfoxide (DMSO) as a stock solution and kept frozen at −20° C. For loading the cells, DCFH-DA from the stock solution was mixed with loading medium (99% RPMI and 1% FBS (fetal bovine serum)) to a final concentration of 20 μM. Standardized aqueous solutions of fractions isolated or derived from hops (Humulus lupulus) were obtained from BetaTech (Washington, D.C.) and are as described in Example 1 Table 1. Positive control compounds included caffeic acid and Trolox obtained from Sigma (St. Louis, Mo.) and were of the highest purity commercially available. Test compounds were dissolved in DMSO to deliver at the maximal concentration in cell cultures of 0.1% (v/v). Unless otherwise noted, all standard reagents were obtained from Sigma and were the purest commercially available.

Cell culture—Jurkat cells (human T cells) were obtained from the American Type Culture Collection (ATCC Number TIB-152, Manassas, Va.) and sub-cultured according to the instructions of the supplier. The cells were routinely cultured at 37° C. with 5% $CO_2$ in RPMI 1640 containing 10% FBS, with 50 units penicillin/mL, 50 μg streptomycin/mL, 5% sodium pyruvate, and 5% L-glutamine.

Jurkat T cells were grown and maintained in RPMI-1640 supplemented with 10% fetal calf serum. 6-Carboxy-2',7'-dichlorofluorescin diacetate (DCFH-DA) was dissolved in dimethyl sulfoxide (DMSO) as a stock solution and kept frozen at −20° C. For incorporating DCFH-DA into cells, exponentially growing cells were treated with DCFH-DA in loading medium (99% RPMI and 1% FBS) at a final concentration of 20 μM for 15 minutes. Excess DCFH-DA was removed by centrifuging the cells for 10 minutes and resuspending them in the original growth medium. Cells were plated in microtiter wells at a concentration of approximately $10^6$ cells per well. Fifteen minutes after the addition of the test compounds, LPS was added in 20 μL to each test well to achieve a final concentration of 1 μg/mL. Twenty μL of LPS-free solution were added to background control wells containing $DCFH_2$-loaded cells. $H_2O_2$ was then added to each well in a volume of 20 μL to achieve final concentrations of 125, 250, 500 or 1000 µM per well. Background cells contained only DCFH-DA and oxidized controls contained DCFH-DA plus LPS and $H_2O_2$. Microtiter plates were placed in a Packard FluoroCount microplate fluorometer equipped with a temperature-controlled plate holder maintained at 37° C. The excitation filter was set at 485 nm and the emission filter was set at 530 nm. Fluorescence for each well was captured, digitized and stored on a computer using Cytofluor (Version 4.0). Measurements of fluorescence were made every ten minutes for 60 minutes. The change in DCF fluorescence is presented relative to the LPS-stimulated Jurkat cells alone; LPS treatment exhibited no increase in fluorescence measurements over the 60-minute experimental period.

The murine macrophage cell line RAW 264.7 was obtained from ATCC (TIB-71) and sub-cultured according to instructions from the supplier. For experiments, cells were cultured in DMEM (Dulbecco's Modification of Eagle's Medium) containing 10% FBS-HI (fetal bovine serum, heat inactivated), with added 50 units penicillin/mL and 50 µg streptomycin/mL, maintained in log phase in T-75 flasks (Corning, Corning, N.Y.) prior to experimental setup. Cells were maintained in a 5% $CO_2$ humidified incubator at 37° C.

For experiments, exponentially growing Jurkat cells were harvested by centrifuging at 6,000 rpm for 10 minutes in 50 mL conical tubes, washing with serum-free RPMI 1640 and centrifuging again at 6,000 rpm. The supernatant fraction from the second centrifugation step was discarded and the cells were resuspended to $1 \times 10^6$ cells/mL for loading with DCFH-DA at a concentration of 20 µM for 30 minutes at 37° C. in 5% $CO_2$. DCFH-DA loading medium was removed by centrifugation; cells were washed with serum-free RPMI medium and aliquoted to microtiter wells at $10^6$ cells per well. Non-$DCFH_2$ control wells (i.e., microtiter wells that do not contain the $DCFH_2$ fluorescent indicator) were made using serum-free RPMI 1640 and DMSO in place of loading medium.

Adherent RAW 264.7 cells were loaded with DCFH-DA at a concentration of 20 µM for 30 minutes at 37° C. in 5% $CO_2$. in the T-75 flask after removing the growth medium. The DCFH-DA medium was discarded and the cells were washed with PBS (phosphate-buffered saline), scrapped and aliquoted to microtiter wells at $10^6$ cells per well. Non-$DCFH_2$ control wells were made using serum-free RPMI 1640 and DMSO in place of loading medium.

Antioxidant activity of the test materials—Oxidative stress was measured in cells using DCFH-DA in a microtiter plate assay as previously described [Wang, H. and Joseph, J. A. (1999) Quantifying cellular oxidative stress by dichlorofluorescein assay using microplate reader. Free Radical Biology & Medicine 27:612-616] incorporated herein by reference. Based upon the conversion of the non-fluorescent 2',7'-dichlorofluorescin ($DCFH_2$) to the highly fluorescent 2',7'-dichlorofluorescein (DCF) by various free radicals, this indiscriminate probe produces concentration dependent changes in cellular fluorescence. Thus, the assay can be used to quantify overall oxidative stress in cells.

Starting at 50 µg/mL, four, serially, diluted concentrations of test material, each in 50 µL, were added to the cells 15 minutes before the LPS (lipopolysaccharide) (1 µg/mL) and $H_2O_2$ (1000 µM) challenge. Caffeic acid and Trolox were added at 12, 6.0, 3.0, and 1.5 µg/mL. DMSO was added to the control wells in an equal volume to that contained with the test compounds and positive controls. Twenty µL of LPS-free solution were added to background control wells containing $DCFH_2$-loaded cells. The microtiter plates containing DCFH-DA-loaded Jurkat or RAW 264.7 cells and test materials were then placed in a Packard FluoroCount, Model BF 10000 fluorometer (Meriden, Conn.) equipped with a temperature-controlled plate holder.

All RFU (relative fluorescence unit) measurements were preformed in a 96-well polypropylene plate with stirring; temperature was maintained at 37° C. The excitation filter was set at 485 nm and the emission filter was set at 530 nm. Fluorescence for each well was captured, digitized and stored on a computer using Cytofluor (Version 4.0). Data points were taken every 10 minutes for 60 minutes. Complete assays were exported to an Excel (Microsoft, Seattle, Wash.) spreadsheet for analysis.

Figure 2:
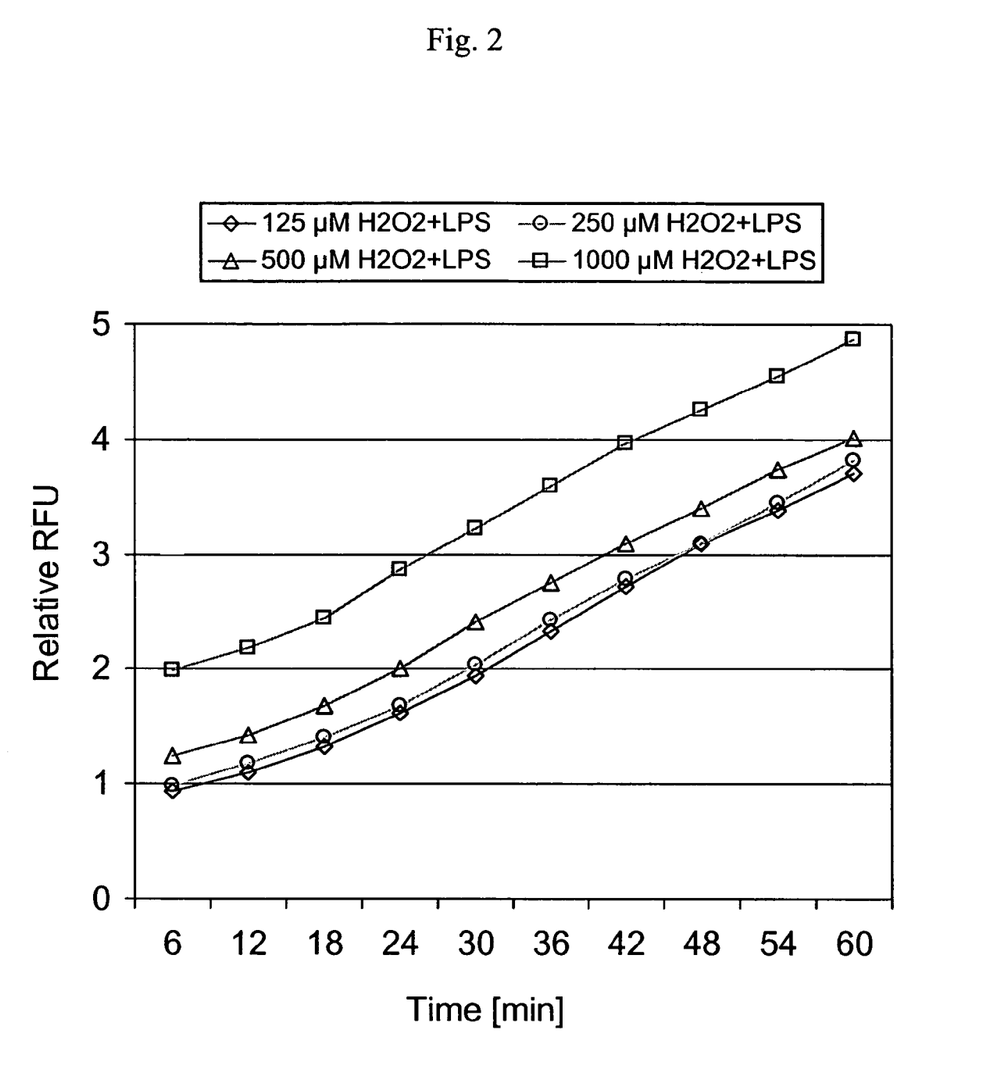
FIG. 2 depicts relative change in DCF fluorescence over time in the Jurkat LPS-$H_2O_2$ oxidative stress model.

FIG. 2 represents the relative RFU for (Cells+$DCFH_2$+$H_2O_2$+LPS/(Cells+$DCFH_2$+LPS) at four concentrations of $H_2O_2$ each with 1 µg/mL LPS. Oxidation of $DCFH_2$ was linear over the 60 minutes for each $H_2O_2$ concentration. Although the slopes of $DCFH_2$ oxidation were similar for all $H_2O_2$ concentrations, a noticeable increase in extent of $DCFH_2$ oxidation was seen at the 1000 µM $H_2O_2$ concentration. This maximum oxidative stress model, 1000 µM $H_2O_2$ plus 1 µg/mL LPS, was selected as the standard for induction of ROI (reactive oxygen intermediate) (used interchangeably with ROS) in the cells.

Data handling and calculation of the median inhibitory concentration ($IC_{50}$)—The extent of oxidation of intracellular $DCFH_2$ during the 60-minute duration of the experiment was expressed as $AUC_{(0-60)}$ (area under curve) and calculated using the trapezoidal method. The area for each 10-minute reading period generated by the increase in RFU over time is trapezoidal. Summation of the area of each trapezoid ($A_{(a-b)}$ = $[0.5*(RFU_b+RFU_a)]*[T_b-T_a]$, where $T_b-T_a$ represents the ten minute interval between RFU readings from 0 to 60 minutes) was used to compute the $AUC_{(0-60)}$.

Inhibition of $DCFH_2$ oxidation by test materials was calculated based upon $AUC_{(Cells+DCFH2+H2O2+LPS)}$=0% inhibition and $AUC_{(Cells+DCFH2)}$=100% inhibition and $AUC_{(Cells)}$= background. The dynamic range of inhibition was defined as the AUC between 0 and 100%=$AUC_{(Cells+DCFH2)}$−$AUC_{(Cells+DCFH2+H2O2+LPS)}$. The fractional inhibition of $DCFH_2$ oxidation by each concentration of test material was calculated as:

$$[AUC_{(Cells+DCFH2+H2O2+LPS+Test\ Sample\ Dose)} - AUC_{(Cells+DCFH2+H2O2+LPS)}][AUC_{(Cells+DCFH2)} - AUC_{(Cells+DCFH2+H2O2+LPS)}]$$

The median inhibitory concentration ($IC_{50}$) and its 95% confidence limits for the inhibition of ROS (reactive oxygen species) were calculated using CalcuSyn (BIOSOFT, biosoft.com). This statistical package performs multiple drug dose-effect calculations using the median effect methods described by T-C Chou and P. Talaly (Trends Pharmacol. Sci. 4:450-454) hereby incorporated by reference. The program correlates the "concentration" and the "effect" in the simplest possible form: fa/fu=$(C/Cm)^m$, where C is the concentration of the compound and Cm is the median-effective concentration signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect curve obtained is a plot of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. Experiments were duplicated and, based upon results of the first assay, concentrations of test material were chosen to capture the median effective dose.

Cell viability—The CellTiter 96® Aqueous One Solution Cell Proliferation Assay (Promega, Madison, Wis.) was used to assess cellular respiration, as a measure of cell viability, following exposure to the test materials and oxidative stressors. The tetrazolium compound [3-(4,5-dimethylthiazol-2-yl)-5-(3-carboxymethoxyphenyl)-2-(4-sulfophenyl)-2H-tetrazolium; MTS] is reduced by NADPH or NADH in living cells into a colored formazan product that is soluble in tissue culture medium. The assay was performed according to the procedure recommended by the manufacturer. MTS reagent was added directly into the microtiter wells, incubated for 1 hour at 37° C. and the absorbance at 490 nm was recorded on a BioTex Instruments ELX-800 microtiter spectrophotometer (Winooski, Vt.). The formazan product as measured at 490 nm is directly proportional to the number of living cells. Cell viability was not affected by the test materials at concentrations used in the assay.

Results

The production of ROI as measured by increased relative RFU over the 60-minute experimental period is shown in FIG. 2. Relative to the LPS-stimulation alone, $H_2O_2$ increased fluorescence 3.7-, 3.8-, 4.0-, and 4.9-fold at 125, 250, 500 and 1000 µM, respectively. Neither LPS nor DMSO produced a change in absolute RFU during the experimental period. Thus, the model selected provided a robust test of antioxidant potential.

Table 5 lists the observed median inhibitory concentrations ($IC_{50}$s) of the hops test materials and positive controls in the Jurkat and RAW 264.7 oxidative stress models. While the positive controls predicatively produced a high degree of antioxidant protection in these models, none of the hops fractions tested exhibited antioxidant activity at any of the doses tested.

TABLE 5

Antioxidant activity of hop materials evaluated in Jurkat and RAW 264.7 cells

| | $IC_{50}$ (µg/mL) | |
|---|---|---|
| a. Test Material | Jurkat $H_2O_2$ + LPS | RAW $H_2O_2$ + LPS |
| Alpha Hop | no activity† | no activity |
| Beta Acids | no activity | no activity |
| Aromahop OE | no activity | no activity |
| Isohop | no activity | no activity |
| Tetrahop Gold (THIAA) | no activity | no activity |
| Redihop | no activity | no activity |
| Hexahop Gold (HHIAA) | no activity | no activity |
| Positive Controls | | |
| Caffeic acid | 3.2 (2.5-4.1) | 3.3 (2.1-5.4) |
| Trolox (Vitamin E activity) | 5.4 (3.1-9.3) | Not tested |

†No antioxidant activity was detected at the highest concentration tested (50 µg/mL).

The absence of significant antioxidant activity for the hop bitter acids tested (Table 5) eliminates the possibility of a trivial antioxidant mechanism for 5-lipoxygenase inhibition observed in Example 1 and suggests a target specific mode of action for the hops derivatives. Additionally, the lack of any observed inhibition of 5-lipoxygenase by the antioxidant caffeic acid implies that the 5-lipoxygenase assay is not affected by antioxidants per se.

EXAMPLE 3

Inhibition of $PGE_2$ Synthesis in Stimulated and Nonstimulated Murine Macrophages by Hops (*Humulus lupulus*) Compounds and Derivatives Summary—This example illustrates the potency of hops fractions and derivatives to inhibit COX-2 synthesis of $PGE_2$ preferentially over COX-1 synthesis of $PGE_2$ in the murine macrophage model.

Chemicals and reagents—Bacterial lipopolysaccharide (LPS; B *E. coli* 055:B5) was from Sigma (St. Louis, Mo.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. Unless otherwise noted, all standard reagents were obtained from Sigma (St. Louis, Mo.) and were the purest commercially available. All other chemicals and equipment were as described in Examples 1 and 2 of U.S. patent application publication number 2004/0086580.

Cell culture—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 mL of heat inactivated FBS and 5 mL of penicillin/streptomycin to a 500 mL bottle of DMEM and storing at 4° C. The growth medium was warmed to 37° C. in water bath before use.

On day one of the experiment, the log phase RAW 264.7 cells were plated at $8 \times 10^4$ cells per well in 0.2 mL growth medium per well in a 96-well tissue culture plate in the morning. At the end of the day one (6 to 8 h post plating), 100 µL of growth medium from each well were removed and replaced with 100 µL fresh medium.

A 1.0 mg/mL stock solution of LPS, used to induce the expression of COX-2 in the RAW 264.7 cells, was prepared by dissolving 1.0 mg of LPS in 1 mL DMSO. It was vortexed until dissolved and stored at 4° C. Before use, it was melted at room temperature or in a 37° C. water bath.

On day two of the experiment, test materials were prepared as 1000× stock in DMSO. In 1.7 mL microfuge tubes, 1 mL DMEM without FBS was added for test concentrations of 0.05, 0.10, 0.5, and 1.0 µg/mL. Two µL of the 1000×DMSO stock of the test material was added to the 1 mL of medium without FBS. The tube contained the final concentration of the test material concentrated 2-fold and the tube placed in an incubator for 10 minutes to equilibrate to 37° C.

For COX-2 associated $PGE_2$ synthesis, 100 µL of medium were removed from each well of the cell plates prepared on day one and replaced with 100 µL of equilibrated 2× final concentration of the test compounds. Cells were then incubated for 90 minutes. Twenty µL of LPS were added to each well of cells to be stimulated to achieve a final concentration of 1 µg LPS/mL and the cells were incubated for 4 h. The cells were further incubated with 5 µM arachidonic acid for 15 minutes. Twenty-five µL of supernatant medium from each well was transferred to a clean microfuge tube for the determination of $PGE_2$ released into the medium.

Following the LPS stimulation, the appearance of the cells was observed and viability was determined as described in Example 2 of U.S. patent application publication number 2004/0086580. No toxicity was observed at the highest concentrations tested for any of the compounds. Twenty-five μL of supernatant medium from each well was transferred to a clean microfuge tube for the determination of $PGE_2$ released into the medium. $PGE_2$ was determined and reported as described in Example 1 of U.S. patent application publication number 2004/0086580.

For COX-1 associated $PGE_2$ synthesis, 100 μL of medium were removed from each well of the cell plates prepared on day one and replaced with 100 μL of equilibrated 2× final concentration of the test compounds. Cells were then incubated for 90 minutes. Next, instead of LPS stimulation, the cells were incubated with 100 μM arachidonic acid for 15 minutes. Twenty-five μL of supernatant medium from each well was transferred to a clean microfuge tube for the determination of $PGE_2$ released into the medium. The appearance of the cells was observed and viability was determined as described in Example 2 of U.S. patent application publication number 2004/0086580. No toxicity was observed at the highest concentrations tested for any of the compounds. Twenty-five μL of supernatant medium from each well was transferred to a clean microfuge tube for the determination of $PGE_2$ released into the medium. $PGE_2$ was determined and reported as previously described in Example 1 of U.S. patent application publication number 2004/0086580. The median inhibitory concentrations ($IC_{50}$) for $PGE_2$ synthesis from both COX-2 and COX-1 were calculated as described in Example 2 of U.S. patent application publication number 2004/0086580.

TABLE 6

COX-2 and COX-1 inhibition in RAW 264.7 cells by hop fractions and derviatives

| Test Material | COX-2 $IC_{50}$ [μg/mL] | COX-1 $IC_{50}$ [μg/mL] | COX-1/COX-2 |
|---|---|---|---|
| Alpha hop (AA) | 0.21 | 6.2 | 30 |
| Aromahop OE | 1.6 | 4.1 | 2.6 |
| Isohop (IAA) | 0.13 | 18 | 144 |
| Beta acids (BA) | 0.54 | 29 | 54 |
| Hexahop (HHIAA) | 0.29 | 3.0 | 11 |
| Redihop (RIAA) | 0.34 | 29 | 87 |
| Tetrahop (THIAA) | 0.20 | 4.0 | 21 |
| Spent hops (EtOH) | 0.88 | 21 | 24 |

As seen in Table 6, all hops fractions and derivative selectively inhibited COX-2 over COX-1 in this target macrophage model. This was a novel and unexpected finding. The extent of COX-2 selectivity for the hops derivatives IAA and RIAA, respectively, 144- and 87-fold, was unanticipated. Such high COX-2 selectivity combined with low median inhibitory concentrations, has not been previously reported for natural products from other sources.

EXAMPLE 4

Reduced Isomerized Alpha Acids Relieve Headache Pain of Allergies

Three adult subjects (one females and two males) with ages ranging from 40 to 57 years) were given a caplet formulation containing 225 mg of reduced isomerized alpha acids per caplet to be taken two times per day. During a following week-long observation period, all subjects reported significant relief from their seasonal allergies. A wash-out period during which no test material was taken caused a return to the headaches suffered from their seasonal allergies in all three subjects. When the test formulation was re-administered, all subjects again reported significant headache relief occurring within 30 minutes of consuming the caplet. This observation indicates the reduced isomerized alpha acid composition of the present invention facilities rapid relief from seasonal allergies.

EXAMPLE 5

IAA and RIAA are not COX-1 or COX-2 Enzyme Inhibitors at Physiologically Relevant Levels

| Indomethacin | | IAA | | RIAA | |
|---|---|---|---|---|---|
| /ml | % Inhibition | ug/ml | % Inhibition | ug/ml | % Inhibition |
| COX 1 | | COX 1 | | COX 1 | |
| 10 | 60.6 | 200 | 9.6 | 200 | 2.9 |
| 1 | 34.6 | 100 | 3 | 100 | 0.5 |
| 0.01 | 28.2 | 10 | 4.2 | 10 | 2.5 |
| 0.001 | −2.8 | 1 | 2.1 | 1 | 1.9 |
| COX 2 | | COX 2 | | COX 2 | |
| 200 | 48.4 | 200 | 0.3 | 200 | 1.9 |
| 50 | 77.6 | 100 | −3.6 | 100 | −0.7 |
| 0.5 | 67.5 | 10 | −2 | 10 | 2.7 |
| 0.05 | 3.4 | 1 | 0.9 | 1 | 2.8 |

Methodology for Example 5

The Cayman Chemical COX Inhibitor Screening Assay Kit (CISAK, cat#560131) was used to assess the effect of test materials directly on the activity of both COX-1 and COX-2 enzymes. One mL aliquots of reaction buffer supplied in the kit were placed on a dry bath at 37° C., and 10 μLs of heme and either the COX-1 or COX-2 enzyme were added to the reaction buffer. Twenty μL of test compound were added, followed by a ten-minute incubation. Arachidonic acid was added to initiate the reaction, which was allowed to proceed for 2 minutes. The reaction was stopped by the addition of 56 μL of 1 M HCL, and the resulting $PGH_2$ was reduced to $PGF_2$, by the addition of 100 μL of stannous chloride. The reduced reaction mixture was allowed to sit at room temperature for 5 minutes, and then was refrigerated until used in the EIA assay. Each reaction was performed in duplicate, and each duplicate was plated on the EIA plate twice.

EIA Assay: The EIA assay was conducted by first preparing a 1:2000 dilution of the reduced reaction products in EIA buffer. Fifty μL of this dilution was added to each sample well of the 96-well EIA plate, followed by the addition of 50 μL of prostaglandin screening tracer (acetylcholineterase conjugated $PGF_{2\alpha}$) and 50 μL of prostaglandin screening antibody. Controls consisted of (1) blanks (left empty until the plate was actually developed), (2) maximum binding controls (containing tracer and antibody, without sample), and (3) non-specific binding controls that contained tracer without antibody. A standard curve was prepared, starting with 1000 pg/mL $PGF_{2\alpha}$, followed by 500 pg/mL, 250 pg/mL, 125 pg/mL, 62.5 pg/mL, 31.2 pg/mL, 15.6 pg/mL, and 7.8 pg/mL concentrations. The plates were incubated at 4° C. for 18 hours. After incubation, the plates were washed in wash buffer five times, then 200 µL Ellmans reagent was added to each well. One well was left as a total activity control, and 5 µL of tracer were added to this well after the addition of the Ellmans reagent. The plates were read at 405 nm after 60-90 minutes of gentle agitation in the dark.

EXAMPLE 6

Mite Dust Allergens Activate $PGE_2$ Biosynthesis in A549 Pulmonary Cells

Summary—This example illustrates that house mite dust allergens can induce $PGE_2$ biosynthesis in pulmonary epithelial cells.

BACKGROUND

Sensitivity to allergens is a problem for an increasing number of consumers. This issue has been complicated by a surprising increase in asthma over the past few years. Asthma suffers are especially sensitive to airborne allergens. Allergy rates are also on the rise. This gives rise to increased awareness of the causes of allergy symptoms and how to decrease the associated discomfort. Approximately 10% of the population become hypersensitized (allergic) upon exposure to antigens from a variety of environmental sources. Those antigens that induce immediate and/or delayed types of hypersensitivity are known as allergens. These include products of grasses, trees, weeds, animal dander, insects, food, drugs, and chemicals. Genetic predisposition of an individual is believed to play a role in the development of immediate allergic responses such as atopy and anaphylaxis whose symptoms include hay fever, asthma, and hives.

Many allergens are protein-based molecules, and these protein allergens can originate from many sources. It has been know for some time that one of the most common sources of allergens in a house is from dust mites. Of course, as is the case with all allergens, only certain people are allergic to dust mite allergens. But this group of people can be quite large in many areas, especially in hot humid areas. For example, in the southeastern United States of America, where it is both hot and humid for much of the year, the incidence of house dust mite allergies in the general population can be as high as 25%. House dust mites thrive in plush carpets, overstuffed upholstery, cushy bed comforters and the like.

Methods

Mite dust allergen isolation—*Dermatophagoides farinae* are the American house dust mite. *D. farinae* were cultured on a 1:1 ratio of Purina Laboratory Chow (Ralston Purina, Co, St. Louis, Mo.) and Fleischmann's granulated dry yeast (Standard Brands, Inc. New York, N.Y.) at room temperature and 75% humidity. Live mites were aspirated from the culture container as they migrated from the medium, killed by freezing, desiccated and stored at 0% humidity. The allergenic component of the mite dust was extracted with water at ambient temperature. Five-hundred mg of mite powder were added to 5 mL of water (1:10 w/v) in a 15 mL conical centrifuge tube (VWR, Rochester, N.Y.), shaken for one minute and allowed to stand overnight at ambient temperature. The next day, the aqueous phase was filtered using a 0.2 µm disposable syringe filter (Nalgene, Rochester, N.Y.). The filtrate was termed mite dust allergen and used to test for induction of $PGE_2$ biosynthesis in A549 pulmonary epithelial cells.

Cell culture and treatment—This experiment involved the human airway epithelial cell line, A549 (American Type Culture Collection, Bethesda, Md.). The cells were cultured and treated as previously described in Example 2. Mite allergen was added to the culture medium to achieve a final concentration of 1000 ng/mL. Twenty-four hours later, the culture medium was sampled for $PGE_2$ concentration.

$PGE_2$ assay—Determination of $PGE_2$ in the culture medium was performed as previously described in Example 1 of U.S. patent application publication number 2004/0086580.

Statistical analysis—Means of eight replicates per treatment were computed using Excel® spreadsheets (Microsoft, Redmond, Wash.).

Results

Mite allergen treatment increased $PGE_2$ biosynthesis 6-fold in A549 cells (1844 pg $PGE_2$/well) relative to the solvent treated controls (304 pg $PGE_2$/well).

EXAMPLE 7

Hops Derivatives Inhibit Mite Dust Allergen Activation of $PGE_2$ Biosynthesis in A549 Pulmonary Cells Summary—This example illustrates that hops derivatives are capable of inhibiting the $PGE_2$ stimulatory effects of mite dust allergens in A549 pulmonary cells.

Methods

The cell line and testing procedures are as described in Example 6. In addition to mite dust allergen, test materials included Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), and (7) tetrahop (tetrahydro-iso-alpha acids THIAA). Test materials at a final concentration of 10 µg/mL were added 60 minutes prior to the addition of the mite dust allergen.

Results

Table 7 depicts the extent of inhibition of $PGE_2$ biosynthesis by hops derivatives in A549 pulmonary cells stimulated by mite dust allergen. All hops derivatives were capable of significantly inhibiting the stimulatory effects of mite dust allergens.

TABLE 7

$PGE_2$ inhibition by hops derviatives in A549 pulmonary epithelial cells stimulated by mite dust allergen

| Test Material | Percent Inhibition of $PGE_2$ Biosynthesis |
| --- | --- |
| Alpha hop (AA) | 81 |
| Aromahop OE | 84 |
| Isohop (IAA) | 78 |
| Beta acids (BA) | 83 |
| Hexahop (HHIAA) | 82 |
| Redihop (RIAA) | 81 |
| Tetrahop (THIAA) | 76 |

In conclusion, it would also be useful to identify a natural formulation of compounds that would inhibit expression of COX-2, inhibit prostaglandin synthesis selectively in target cells, or inhibit inflammation response selectively in target cells.

A preferred embodiment comprises compositions containing at least one fraction isolated or derived from hops (*Humu-*

*lus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of fractions isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

The invention claimed is:

1. A method of treating an inflammatory condition in a mammal in need thereof, the method comprising administering to the mammal in need thereof a composition comprising a therapeutically effective amount of a compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone and hexahydro-isoadhumulone.

2. The method of claim 1, wherein the compound is derived from hops.

3. The method of claim 1, wherein the inflammatory condition is cancer.

4. The method of claim 3, wherein the cancer is breast cancer.

5. The method of claim 3, wherein the cancer is prostate cancer.

6. The method of claim 3, wherein the cancer is colon cancer.

7. The method of claim 3, wherein the cancer is pancreatic cancer.

8. The method of claim 1, wherein the inflammatory condition is asthma.

9. The method of claim 1, wherein the inflammatory condition is Alzheimer's Disease.

10. The method of claim 1, wherein the inflammatory condition is arthritis.

11. The method of claim 1, wherein the inflammatory condition is Crohn's Disease.

12. The method of claim 1, wherein the inflammatory condition is eczema.

13. The method of claim 1, wherein the inflammatory condition is Inflammatory Bowel Disease.

14. The method of claim 1, wherein the inflammatory condition is osteoarthritis.

15. The method of claim 1, wherein the inflammatory condition is psoriasis.

* * * * *